(12) United States Patent
Hatlestsad et al.

(10) Patent No.: US 7,226,422 B2
(45) Date of Patent: Jun. 5, 2007

(54) DETECTION OF CONGESTION FROM MONITORING PATIENT RESPONSE TO A RECUMBENT POSITION

(75) Inventors: John Hatlestsad, Maplewood, MN (US); Qingsheng Zhu, Little Canada, MN (US); Jeffrey E Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 362 days.

(21) Appl. No.: 10/267,982

(22) Filed: Oct. 9, 2002

(65) Prior Publication Data

US 2004/0073128 A1   Apr. 15, 2004

(51) Int. Cl.
A61B 5/05 (2006.01)
A61B 5/08 (2006.01)

(52) U.S. Cl. .................. 600/534; 600/547

(58) Field of Classification Search .......... None
See application file for complete search history.

(56) References Cited

U.S. PATENT DOCUMENTS

| | | |
|---|---|---|
| 4,003,379 A | 1/1977 | Ellinwood, Jr. |
| 4,059,169 A | 11/1977 | Hagen |
| 4,271,192 A | 6/1981 | Wurtman et al. |
| 4,308,872 A * | 1/1982 | Watson et al. ........... 600/538 |
| 4,470,987 A | 9/1984 | Wurtman et al. |
| 4,559,946 A | 12/1985 | Mower |
| 4,562,843 A | 1/1986 | Djordjevich et al. |
| 4,567,892 A | 2/1986 | Plicchi et al. |
| 4,576,183 A | 3/1986 | Plicchi et al. |

(Continued)

FOREIGN PATENT DOCUMENTS

EP    348271    12/1989

(Continued)

OTHER PUBLICATIONS

C. Lucas, M.D., W. Johnson, M.D., M. Hamilton, M.D., G. Fonarow, M.D., M. Woo, D.N.S., C. Flavell, M.S., J. Creaser, M.N., and L. Stevenson, M.D., "Congestive Heart Failure, Freedom from Congestion Predicts Good Survival Despite Previous Class IV Symptons of Heart Failure,", *American Heart Journal*, Dec. 2000; vol. 140, No. 6, p. 840-847.

(Continued)

*Primary Examiner*—Robert L. Nasser
(74) *Attorney, Agent, or Firm*—Schwegman, Lundberg, Woessner, & Kluth

(57) ABSTRACT

Systems and methods obtain information that allows detection of whether a patient suffers from congestion by monitoring a response of the patient to a recumbent position of the patient's body. The patient may be monitored to determine a respiration pattern for a non-recumbent position such as standing and a respiration pattern for a recumbent position such as lying down. The two patterns may be compared, either by a processing device or a physician, to determine a difference in the two respiration patterns. Furthermore, the congestion may be inferred from detecting an amount of time that the patient spends in a recumbent position of from detecting the recumbent angle that the patient obtains, either of which is presumed to indicate whether a recumbent position presents discomfort to the patient due to the presence of congestion.

26 Claims, 7 Drawing Sheets

U.S. PATENT DOCUMENTS

| | | | |
|---|---|---|---|
| 4,651,716 A | 3/1987 | Forester et al. | |
| 4,693,253 A | 9/1987 | Adams | |
| 4,880,005 A | 11/1989 | Pless et al. | |
| 4,884,576 A | 12/1989 | Alt | |
| 4,904,472 A | 2/1990 | Belardinelli et al. | |
| 4,980,379 A | 12/1990 | Belardinelli et al. | |
| 4,987,897 A | 1/1991 | Funke | |
| 5,002,052 A | 3/1991 | Haluska | |
| 5,003,976 A | 4/1991 | Alt | |
| 5,025,786 A | 6/1991 | Siegel | |
| 5,040,536 A | 8/1991 | Riff | |
| 5,113,869 A | 5/1992 | Nappholz et al. | |
| 5,117,825 A | 6/1992 | Grevious | |
| 5,199,428 A | 4/1993 | Obel et al. | |
| 5,213,098 A | 5/1993 | Bennett et al. | |
| 5,215,083 A | 6/1993 | Drane et al. | |
| 5,233,984 A | 8/1993 | Thompson | |
| 5,233,985 A | 8/1993 | Hudrlik | |
| 5,246,008 A | 9/1993 | Mueller | |
| 5,271,395 A | 12/1993 | Wahlstrand et al. | |
| 5,273,034 A | 12/1993 | Nilsson | |
| 5,282,836 A | 2/1994 | Kreyenhagen et al. | |
| 5,282,840 A | 2/1994 | Hudrlik | |
| 5,284,136 A | 2/1994 | Hauck et al. | |
| 5,292,343 A | 3/1994 | Blanchette et al. | |
| 5,300,093 A | 4/1994 | Koestner et al. | |
| 5,313,953 A | 5/1994 | Yomtov et al. | |
| 5,324,309 A | 6/1994 | Kallok | |
| 5,324,315 A | 6/1994 | Grevious | |
| 5,342,404 A | 8/1994 | Alt et al. | |
| 5,344,429 A | 9/1994 | Smits | |
| 5,354,317 A | 10/1994 | Alt | |
| 5,354,319 A | 10/1994 | Wyborny et al. | |
| 5,355,894 A | 10/1994 | Sivard | |
| 5,366,485 A | 11/1994 | Kroll et al. | |
| 5,370,665 A | 12/1994 | Hudrlik | |
| 5,404,877 A | 4/1995 | Nolan et al. | |
| 5,405,362 A | 4/1995 | Kramer et al. | |
| 5,411,031 A | 5/1995 | Yomtov | |
| 5,431,682 A | 7/1995 | Hedberg | |
| 5,441,525 A | 8/1995 | Shelton et al. | |
| 5,454,377 A | 10/1995 | Dzwonczyk et al. | |
| 5,464,434 A | 11/1995 | Alt | |
| 5,479,369 A | 12/1995 | Matsumura et al. | |
| 5,501,701 A | 3/1996 | Markowitz et al. | |
| 5,507,785 A | 4/1996 | Deno | |
| 5,522,860 A | 6/1996 | Molin et al. | |
| 5,534,018 A | 7/1996 | Wahlstrand et al. | |
| 5,540,728 A | 7/1996 | Shelton et al. | |
| 5,562,711 A | 10/1996 | Yerich et al. | |
| 5,562,712 A | 10/1996 | Steinhaus et al. | |
| 5,593,431 A | 1/1997 | Sheldon | 607/19 |
| 5,626,623 A | 5/1997 | Kieval et al. | |
| 5,676,686 A | 10/1997 | Jensen et al. | |
| 5,706,829 A | 1/1998 | Kadri | |
| 5,722,999 A | 3/1998 | Snell | |
| 5,725,561 A | 3/1998 | Stroebel et al. | |
| 5,725,562 A | 3/1998 | Sheldon | |
| 5,732,710 A | 3/1998 | Rabinovich et al. | |
| 5,749,369 A | 5/1998 | Rabinovich et al. | |
| 5,749,900 A | 5/1998 | Schroeppel et al. | |
| 5,782,879 A | 7/1998 | Rosborough et al. | |
| 5,788,643 A | 8/1998 | Feldman | |
| 5,800,464 A | 9/1998 | Kieval | |
| 5,874,420 A | 2/1999 | Pelleg | |
| 5,876,353 A | 3/1999 | Riff | |
| 5,913,879 A | 6/1999 | Ferek-Petric et al. | |
| 5,919,210 A | 7/1999 | Lurie et al. | |
| 5,957,861 A | 9/1999 | Combs et al. | 600/547 |
| 5,957,957 A | 9/1999 | Sheldon | 607/17 |
| 5,978,705 A | 11/1999 | KenKnight et al. | |
| 6,002,963 A | 12/1999 | Mouchawar et al. | 607/18 |
| 6,015,388 A * | 1/2000 | Sackner et al. | 600/529 |
| 6,035,233 A | 3/2000 | Schroeppel et al. | |
| 6,044,297 A | 3/2000 | Sheldon et al. | 607/17 |
| 6,047,203 A | 4/2000 | Sackner et al. | 600/388 |
| 6,049,730 A | 4/2000 | Kristbjarnarson | |
| 6,049,735 A | 4/2000 | Hartley et al. | |
| 6,076,015 A | 6/2000 | Hartley et al. | |
| 6,078,834 A | 6/2000 | Lurie et al. | |
| 6,104,949 A | 8/2000 | Pitts Crick et al. | 600/547 |
| 6,154,672 A | 11/2000 | Pendekanti et al. | |
| 6,298,267 B1 | 10/2001 | Rosborough et al. | |
| 6,317,631 B1 | 11/2001 | Ben-Haim et al. | |
| 6,336,903 B1 | 1/2002 | Bardy | |
| 6,411,844 B1 | 6/2002 | Kroll et al. | |
| 6,473,640 B1 | 10/2002 | Erlebacher | |
| 6,512,949 B1 | 1/2003 | Combs et al. | |
| 6,574,506 B2 | 6/2003 | Kramer et al. | |
| 6,595,927 B2 | 7/2003 | Pitts-Crick et al. | |
| 6,616,607 B2 | 9/2003 | Hashimoto et al. | |
| 6,625,492 B2 | 9/2003 | Florio et al. | |
| 6,665,564 B2 | 12/2003 | Lincoln et al. | |
| 6,678,547 B2 | 1/2004 | Carlson et al. | |
| 6,719,701 B2 | 4/2004 | Lade | |
| 6,738,666 B1 | 5/2004 | Park et al. | |
| 6,748,271 B2 | 6/2004 | Spinelli et al. | |
| 6,752,765 B1 * | 6/2004 | Jensen et al. | 600/536 |
| 6,811,537 B2 | 11/2004 | Bardy | |
| 6,829,503 B2 | 12/2004 | Alt | |
| 6,829,507 B1 | 12/2004 | Lidman et al. | |
| 6,912,420 B2 | 6/2005 | Scheiner et al. | |
| 6,937,900 B1 | 8/2005 | Pianca et al. | |
| 6,949,075 B2 | 9/2005 | Hatlesad et al. | |
| 2002/0123674 A1 | 9/2002 | Plicchi et al. | |
| 2002/0147475 A1 | 10/2002 | Scheiner et al. | |
| 2002/0170193 A1 | 11/2002 | Townsend et al. | |
| 2003/0055461 A1 | 3/2003 | Girouard et al. | |
| 2003/0105496 A1 | 6/2003 | Yu et al. | |
| 2003/0144595 A1 | 7/2003 | Lade | |
| 2003/0176896 A1 | 9/2003 | Lincoln et al. | |
| 2003/0220580 A1 | 11/2003 | Alt | |
| 2004/0073128 A1 | 4/2004 | Hatlestad et al. | |
| 2004/0102712 A1 | 5/2004 | Belalcazar et al. | |
| 2004/0106962 A1 | 6/2004 | Mai et al. | |
| 2004/0116819 A1 | 6/2004 | Alt | |
| 2004/0133079 A1 | 7/2004 | Mazar et al. | |
| 2004/0147982 A1 | 7/2004 | Bardy | |
| 2004/0172080 A1 | 9/2004 | Stadler et al. | |
| 2004/0215097 A1 | 10/2004 | Wang | |
| 2004/0215270 A1 | 10/2004 | Ritscher et al. | |
| 2005/0004609 A1 | 1/2005 | Stahmann et al. | |
| 2005/0038327 A1 | 2/2005 | Tanaka et al. | |
| 2005/0080460 A1 | 4/2005 | Wang et al. | |
| 2005/0283197 A1 | 12/2005 | Daum et al. | |
| 2006/0020295 A1 | 1/2006 | Brockway et al. | |
| 2006/0025699 A1 | 2/2006 | Maile et al. | |

FOREIGN PATENT DOCUMENTS

| | | |
|---|---|---|
| EP | 0584388 A1 | 3/1994 |
| EP | 0620420 | 10/1994 |
| EP | 0663219 A1 | 7/1995 |
| EP | 0985374 A2 | 3/2000 |
| EP | 0985429 | 3/2000 |
| EP | 1151719 | 11/2001 |
| EP | 1238630 A2 | 9/2002 |
| EP | 1115350 B1 | 8/2003 |
| EP | 1011803 B1 | 9/2004 |
| EP | 0985374 B1 | 12/2004 |
| EP | 0985429 B1 | 12/2004 |
| WO | WO-8400227 | 1/1984 |
| WO | WO-9800197 A1 | 1/1998 |
| WO | WO-9833554 A1 | 8/1998 |

| | | |
|---|---|---|
| WO | WO-0018317 A2 | 4/2000 |
| WO | WO 0119426 | 3/2001 |
| WO | WO-2004012815 A1 | 2/2004 |
| WO | WO-04047638 A1 | 6/2004 |
| WO | WO-2004050178 A1 | 6/2004 |
| WO | WO-04060166 A2 | 7/2004 |
| WO | WO-04095306 A1 | 11/2004 |
| WO | WO-05046472 A1 | 5/2005 |

OTHER PUBLICATIONS

"Heart Sounds", http://www.chfpatients.com/fag/s3s4.htm.

"Medtronic Announces European Release Of Innovative InSync Sentry Cardiac Resynchronization Therapy Defibrillator", http://www.medtronic.com/newsroom/news_20040614a.html, (2004).

"Medtronic: InSync Sentry 7298: Dual Chamber Implantable Cardioverter Defibrillator with Cardiac Resynchronization Therapy (VVE-DDR) and Opti-Vol Fluid Monitoring: Reference Manual", www.medtronic.com.

Adamicza, A., et al., "Changes in transthoracic electrical impedance during endotoxemia in dogs", *Acta Physiol Hung.*, 85(4), (1997-98),291-302.

Adamicza, A., et al., "Investigation of the thoracic electrical impedance during endotoxemia in dogs", *Acta Chir Hung.*, 36(1-4), (1997), 1-3.

Alt, Eckhard, et al., "Control of Pacemaker Rate by Impedance-based Respiratory Minute Ventilation*", *Chest*, 92(2), (Aug. 1987),247-252.

Baarends, E. M., et al., "Body-water compartments measured by bio-electrical impedance spectroscopy in patients with chronic obstructive pulmonary disease", *Clinical Nutrition*, 17(1), (Feb. 1998), 15-22.

Belalcazar, Andres, et al., "Improved lung edema monitoring with coronary vein pacing leads", *Pacing and Clinical Electrophysiology*, 26(4 pt. II), Abstract 18,(Apr. 2003),933.

Belalcazar, Andres, et al., "Improving lung edema monitoring with coronary vein pacing leads: a simulation study", *Physiological Measurement*, vol. 25, (2004),475-487.

Berman, Irwin R., et al., "Transthoracic electrical impedance s a guide to intravascular overload", *Archives of Surgery*, 102(1), (Jan. 1971),61-64.

Bradbury, M. G., et al., "Assessment of the sensitivity of bioimpedance to volume changes in body water", *Pediatr Nephrol.*, 9(3), (Jun. 1995),337-40.

Campbell, J. H., et al., "Clinical applications of electrical impedance tomography in the monitoring of changes in intrathoracic fluid volumes", *Physiol. Meas.*, vol. 15, (1994),A217-A222.

Campbell, J. H., et al., "Detection of changes in intrathoracic fluid in man using electrical impedance tomography", *Clinical Science*, vol. 87, (1994),97-101.

Charach, Gideon, et al., "Transthoracic monitoring of the impedance of the right lung in patients with cardiogenic pulmonary edema", *Critical Care Medicine*, 29(6), (Jun. 2001), 1137-44.

Chiolero, R. L., et al., "Assessment of changes in body water by bioimpedance in acutely ill surgical patients", *Intensive Care Medicine*, 18(6), (1992),322-6.

Daum, Douglas R., "Systems and Methods for Hypotension", U.S. Appl. No. 11/141,260, filed May 31, 2005, 51 pages.

Defaye, P., et al., "Automatic Recognition of Abnormal Respiratory Events During Sleep by a Pacemaker Transthoracic Impedance Sensor", *Journal of Cardiovascular Electrophysiology*, 15(9), (Sep. 2004), 1034-40.

Denniston, J. C., et al., "Factors Influencing the measurement of stroke volume by elelctrical impedance", *Physiology* (1372-1377), Abstract No. 1373,463.

Denniston, J. C., et al., "Measurement of pleural effusion by electrical impedance.", *Journal of Applied Physiology*, 38(5), (May 1975),851-7.

Ellenbogen, Kenneth A., et al., *Clinical Cardiac Pacing*, Philadelphia : Saunders, (1995),22-23.

Ellenbogen, Kenneth A., et al., *Clinical Cardiac Pacing*, Philadelphia : Saunders, (1995),219-233.

Fein, Alan, et al., "Evaluation of Transthoracic Electrical Impedance in the Diagnosis of Pulmonary Edema", *Circulation*, 60(5), (Nov. 1979), 1156-1160.

Forman, B, et al., "Intra-thoracic impedance: a surrogate measure of thoracic fluid - fluid accumulation status trial (FAST)", *Journal of Cardiac Failure*, 10(4 Suppl), Abstract 251, (2004),S86.

Forro, M., et al., "Total body water and ECFV measured using bioelectrical impedance analysis and indicator dilution in horses", *Journal of Applied Physiology*, 89(2), (Aug. 2000),663-71.

Frerichs, I., et al., "Electrical impedance tomography in monitoring experimental lung injury", *Intensive Care Med.*, 24(8), (Aug. 1998),829-36.

Garland, J. S., et al., "Measurement of extravascular lung water in hemodialysis patients using blood ultrasound velocity and optical density dilution.", *ASAIO Journal 2002* 48(4), (Jul-Aug. 2002),398-403.

Goovaerts, H. G., et al., "Microprocessor-based system for measurement of electrical impedances during haemodialysis and in postoperative care", *Medical & Biological Engineering & Computing*, vol. 26, (Jan. 1988),75-80.

Gotshall, R W., et al., "Bioelectric impedance as an index of thoracic fluid.", *Aviation Space and Environmental Medicine*, 70(1), (Jan. 1999),58-61.

Grimbert, F., et al., "Pulmonary water and thoracic impedance. Evaluation of a measurement technic", *Annales de L'anesthésiologie Française*, 16 Spec No. 2-3, French, (1975), 157-63.

Harris, N. D., et al., "Applications of applied potential tomography (APT) in respiratory medicine", *Clinical Physics and Physiological Measurement*, 8 Suppl A, (1987), 155-65.

Hoon, Raghunath S., et al., "Changes in Transthoracic electrical impedance at high altitude", *British Heart Journal*, vol. 39, (1977),61-66.

Hull, E. T., et al., "The Transthoracic Impedance Method for the Determination of the Degree and Change in Extravascular Water", *Acta Tuberc. Pneumol. Belg.*, 68(4), (1977),369-377.

Hull, E. T., et al., "Transthoracic electrical impedance: artifacts associated with electrode movement", *Resuscitation*, 6(2), (1978), 115-124.

Ishibe, Y., et al., "Transthoracic electrical impedance method for measurement of pulmonary edema in vivo", *Masui*: 27(13), Japanese, (Dec. 1978), 1559-67.

Joekes, A. M., et al., "Impedance Cardiography - Its value in an intensive care unit", *D) Materials et techniques/Cardiocirculatory Equipment and Technics*, Abstract No. 141, 1 Page.

Keller, Guido, et al., "Monitoring of Pulmonary Fluid Volume and Stroke Volume by Impedance Caridography in Patients on Hemodialysis", *Chest*, 72(1), (Jul. 1977),56-62.

Khan, Mahfooz R., et al., "Quantitative electrical-impedance plethysmography for pulmonary oedema", *Medical & Biological Engineering & Computing*, vol. 15, (Nov. 1977),627-633.

Kiesler, T. W., et al., "Impedance cardiography by use of a spot-electrode array to track changes in cardiac output in anesthetized dogs.", *Journal of the American Veterinary Medical Association*, 196(11), (Jun. 1, 1990), 1804-10.

Koizumi, T., "Changes of transthoracic impedance (zinf 0 and deltaz) in newborn infants", *Acta Neonatol. Jpn.*, 14(3), (1978),335-340.

Kunst, P. W., et al., "Electrical impedance tomography in the assessment of extravascular lung water in noncardiogenic acute respiratory failure", *Chest*, 116(6), (Dec. 1999), 1695-702.

Kusumoto, Fred M., et al., "Medical Progress: Cardiac Pacing", *New England Journal of Medicine*, 334(2), (Jan. 11, 1996),89-98.

Larsen, F., et al., "Influence of furosemide and body posture on transthoracic electrical impedance in AMI", *Chest*, 90(5), (733-7),Nov. 1986.

Lau, C P., et al., "Rate-responsive pacing with a pacemaker that detects respiratory rate (Biorate): clinical advantages and complications", *Clinical Cardiology*, 11(5), (May 1988),318-24.

Lau, C. P., "The range of sensors and algorithms used in rate adaptive cardiac pacing", *Pacing and clinical electrophysiology: PACE*, 15(8), (Aug. 1992), 1177-211.

Leung, Zoe K., et al., "Feasibility of an automatic atrial and ventricular threshold determination using thransthoracic using impedance", *Pacing and Clinical Eletrophysiology*, vol. 19, Part II, Abtract 263, (Apr. 1996),631.

Luepker, R. V., et al., "Transthoracic Electrical Impedance: Quantitative Evaluation of a Non-Invasive Measure of Thoracic Fluid Volume", *American Heart Journal*, 85(1), (Jan. 1973),83-93.

Mai, J., et al., "Enhanced Rate Response Algorithm for Orthostatic Compensation Pacing", *Pacing Clin Electrophysiol*, 23, Naspe Abstracts, Abstract No. 678,(Apr. 2000),722.

McCarty, Richard N., et al., "Assessment of pulmonary edema in acute congestive heart failure with impedance cardiography", *J Am Osteopath Assoc.*, 74(9), (May 1975),879.

McNamee, James E., et al., "Peribronchial electrical admittance measures lung edema and congestion in the dog", *Special Communications, Electrical Admittance and Pulmonary Edema*, 337-341.

Newell, J. C., et al., "Assessment of acute pulmonary edema in dogs by electrical impedance imaging", *IEEE Transactions on Biomedical Engineering*, 43(2), (Feb. 1996), 133-138.

Nierman, D. M., et al., "Evaluation of transthoracic bioelectrical impedance analysis in monitoring lung water during diuresis", *Applied Cardiopulmonary Pathophysiology*, 7(1), (1997),57-62.

Nierman, David M., et al., "Transthoracic Bioimpedance Can Measure Extravascular Lung Water in Acute Lung Injury1", *Journal of Surgical Research 65*, Article No. 0350, (1996), 101-108.

Noble, T. J., et al., "Diuretic induced change in lung water assessed by electrical impedance tomography", *Physiol Meas.*, 21(1), (Feb. 2000), 155-63.

Nukiwa, Toshihiro, et al., "Responses of Serum and Lung Angiotensin-Converting Enzyme Activities in the Early Phase of Pulmonary Damage Induced by Oleic Acid in Dogs", *Am Rev Respir Dis.*, 126(6), (Dec. 1982), 1080-1086.

Petersen, J. R., et al., "Electrical impedance measured changes in thoracic fluid content during thoracentesis", *Clin Physiol.*, 14(4), (Jul. 1994),459-66.

Platia, Edward V., et al., "Time Course of Transvenous Pacemaker Stimulation Impedance, Capture Threshold, and Electrogram Amplitude", *Pacing Clin Electrophysiol.*, 9(5), (Sep./Oct. 19),620-625.

Pomerantz, M, et al., "Transthoracic electrical impedance for the early detection of pulmonary edema", *Surgery*, 66(1), (Jul. 1969),260-8.

Raaijmakers, E., et al., "Estimation of non-cardiogenic pulmonary oedema using dual-frequency electrical impedance.", *Medical & Biological Engineering & Computing*, 36(4), (Jul. 1998),461-6.

Raggueneau, J. L., et al., "Monitoring of intracellular and extracellular hydric compartments by body impedance", *Anesth Anal. Rean*, vol. 36, (1979),439-443.

Ramos, Marcos U., et al., "Transthoracic electric impedance. A clinical guide of pulmonary fluid accumulation in congestive heart failure", *Minnesota Medicine*, 58(9), (Sep. 1975),671-676.

Rosborough, John P., et al., "Electrical Therapy for Pulseless Electrical Activity", *NASPE*, 23(4), Part II, Abstract,(Apr. 2000),591.

Saunders, Charles E., "The Use of Transthoracic Electrical Bioimpedance in Assessing Thoracic Fluid Status in Emergency Department Patients", *American Journal of Emergency Medicine*, 6(4), (Jul. 1988),337-340.

Schuster, C. J., et al., "Application of Impedance Cardiography in Critical Care Medicine", *Resuscitation*, vol. 11, (1984),255-274.

Schwartzman, David, et al., "Serial Defibrillation Lead Impedance in Patients with Epicardial and Nonthoracotomy Lead Systems", *Journal of Cardiovascular Electrophysiology*, 7(8), (Aug. 1996),697-703.

Segev, Gil, et al., "B-Type Natriuretic Peptide: A Novel Clinical Tool for Diagnosis and Management of Heart Failure", www.turner-white.com, Article in Sep. 2003 "Hospital Physician" magazine., (Sep. 2003), 19-24.

Shochat, M., et al., "Internal thoracic impedance monitoring: a new prospect in acute heart failure", *European Heart Journal*, 25(Supp), (Aug.-Sep. 2004), p. 72-72.

Shoemaker, William C., et al., "Multicenter trial of a new thoracic electrical bioimpedance device for cardiac output estimation", *Critical Care Medicine*, 22(12), (Dec. 1994), 1907-1912.

Smith, R. M., et al., "Canine thoracic electrical impedance with changes in pulmonary gas and blood volumes.", *Journal of Applied Physiology*, 53(6), (Dec. 1982), 1608-13.

Spinale, F. G., et al., "Noninvasive estimation of extravascular lung water using bioimpedance.", *The Journal of Surgical Research*, 47(6), (Dec. 1989),535-40.

Spinelli, J. C., "Method and System for Treatment of Neurocardiogenic Syncore", U.S. Appl. No. 10/862,831, filed Jun. 7, 2004, 15 pages.

Stadler, R., et al., "Automated detection of decreases in intrathoracic impedance to predict CHF hospitalization", Abstract 263, 26(4pt II), Abstract 16, (Apr. 2003),932.

Staub, N. C., "The measurement of lung water content", *The Journal of Microwave Power*, 18(3), (Sep. 1983),259-63.

Tang, W., "Assessment of total body water using bioelectrical impedance analysis in neonates receiving intensive care", *Arch Dis Child Fetal Neonatal Ed.*, 77(2), (Sep. 1997),F123-6.

Tempel, G., et al., "Transthoracic electrical impedance in anaesthesia and intensive care.", *Resuscitation*, 6(2), (1978),97-105.

Thakur, Ranjan K., et al., "Pericardial Effusion Increases Defibrillation Energy Requirement", *Pacing Clin Electrophysiol.*, 16(6), (Jun. 1993), 1227-1230.

Vainshtein, G. B., et al., "The Functioning of the Cerebral Circulation System in Hyperthermia in Rabbits", *Fiziol Zh SSSR Im I M Sechenova*, 75(11), (Nov. 1989), 1608-1614.

Van De Water, Joseph M., et al., "Monitoring the Chest with Impedance", *Chest*, 64(5), (Nov. 1973),597-603.

Viirola, H, "Controlled growth of antimony-doped tin dioxide thin films by atomic layer epitaxy", *Thin Solid Films*, 251, (Nov. 1994), 127-135.

Viirola, H, et al., "Controlled growth of tin dioxide thin films by atomic layer epitaxy", *Thin Solid Films*, 249(2), (Sep. 1994), 144-149.

Visokay, M R., "Application of HfSiON as a gate dielectric material", *Applied Physics Letters*, 80(17), (Apr. 2002),3183-3185.

Wang, L., et al., "Impedance based prediction of CHF admission precedes symptoms in heart failure patients", *Heartrhythm : the offical journal of the Heart Rhythm Society*, 1(Suppl 1), Abstract 679, (2004),S213.

Wang, Li, et al., "Multiple Sources of the Impedance Cardiogram Based on 3-D Finite Difference Human Thorax Models", *IEEE Transactions on Biomedical Engineering*, 42(2), (Feb. 1995), 141-148.

Wang, L., et al., "Prediction of CHF hospitalization by ambulatory intrathoracic impedance measurement in CHF patients is feasible using pacemaker or ICD lead systems", *Pacing and Clinical Electrophysiology*, 26(4 pt. II), Abstract 123, (Apr. 2003),959.

Wuerz, Richard C., et al., "Effects of prehospital medications on mortality and length of stay in congestive heart failure", *Annals of Emergency Medicine*, 21(6), (Jun. 1992),699-74.

Yu, C., et al., "Changes in device based thoracic impedance in decompensating congestive heart failure", *Circulation*, 104(17 supplement)., Abstract 1994,(2001),II-419.

Yu, C. M., et al., "Correlation of device-based intra-thoracic impedance and patient fluid status during intravenous diuretic therapy in acute CHF", *Euopean Heart Journal*, 23(Abstract Supplement), (2002), 158.

Yu, C., et al., "Device-based intra-thoracic impedance correlates with fluid status and provides automaticed prediction of CHF hospitalization", *Journal of Cardiac Failure*, 10(4 Suppl), Abstract 354,(2004),S113.

Yu, Cheuk-Man, et al., "Early warning of CHF hospitalization by intra-thoracic impedance measurement in CHF patients with pacemakers", *Pacing and Clinical Electrophysiology*, 24, (Apr. 2001), 19.

Yu, C., et al., "Early warning of CHF hospitalization by intra-thoracic impedance measurement in CHF patients with pacemakers", *Pacing and Clinical Electrophysiology: PACE*, 24(4 pt II), Abstract 19,(2002),527.

Yu, C. M., et al., "Impedance measurements from implanted devices provide automated prediction of CHF hospitalization", *European Heart Journal*, 25(Supp), (Aug.-Sep. 2004), p. 27-27.

Yu, C. M., et al., "Intrathoracic impedance: A surrogate measure of fluid retention and predictor of hospitalization in patients with heart failure", *Journal of the American College of Cardiology*, 41(6 Supplement A), Abstract 1206-70, (2003),210A.

Zellner, J. L., et al., "Bioimpedance: a novel method for the determination of extravascular lung water.", *The Journal of Surgical Research*, 48(5), (May 1990),454-9.

Zima, E., "Intracardiac impedance in biventricular electrode configuration for left ventricular volume monitoring", *European Heart Journal*, 25(Supp), (Aug.-Sep. 2004), p. 165-165.

Aaron, S. D., et al., "How accurate is spirometry at predicting restrictive pulmonary impairment?", *Chest*, 115(3), (Mar. 1999), 869-873.

Cooke, W. H., et al., "Human responses to upright tilt: a window on central autonomic integration", *J Physiol.*, 517(Pt 2), (Jun. 1, 1999), 617-28.

Hatlestad, John D., et al., "Physiological Response To Posture Change", U.S. Appl. No. 11/466,925, filed Aug. 24, 2006, 21 pages.

Kubo, S. H., et al., "Circulatory autoregulation in chronic congestive heart failure: responses to head-up tilt in 41 patients.", *Am J Cardiol.*, 52(5), (Sep. 1, 1983), 512-8.

Laszlo, Z., et al., "Cardiovascular and Hormonal Changes with Different Angles of Head-up Tilt in Men", *Physiol. Res.*, vol. 50, (2001), 71-82.

Levine, T. B., et al., "The neurohumoral and hemodynamic response to orthostatic tilt in patients with congestive heart failure.", *Circulation*, 67(5), (May 1983), 1070-5.

Miyamoto, S., et al., "Effects of posture on cardiac autonomic nervous activity in patients with congestive heart failure.", *J Am Coll Cardiol.*, 37(7), (Jun. 1, 2001), 1788-93.

Stevenson, L. W., et al., "The limited reliability of physical signs for estimating hemodynamics in chronic heart failure", *JAMA.*, 261(6), (Feb. 19, 1989), 884-8.

* cited by examiner

DETECTION OF CONGESTION FROM MONITORING PATIENT RESPONSE TO A RECUMBENT POSITION

TECHNICAL FIELD

The present invention is related to the detection of congestion of a patient. More particularly, the present invention is related to the detection of congestion through monitoring a patient's response to a recumbent position of the patient's body.

BACKGROUND

A patient suffers from congestion when filling pressure of the heart, which results from the return of blood from the body to the heart, is relatively high due to the heart's inability to effectively pump blood back out to the body. Thus, congestion is indicative of heart failure and is one factor that should be closely monitored for a heart failure patient. Congestion may be manifested in several ways in the heart failure patient's body.

One condition highly correlated with congestion is respiratory distress upon lying down. Congestion often results in the lungs becoming partially filled with fluid once the patient lies down, and the lungs maintain the partially filled state until the patient becomes upright. This filling causes the patient to have difficulty breathing while in the recumbent position, and the respiratory distress that may result from the lungs remaining filled with fluid is a good indicator of congestion.

Attempts have been made to assess congestion from observation of a patient's posture relative to his average trans-thoracic impedance, which decreases as the lungs fill with fluid. However, the average trans-thoracic impedance masks any change that might occur in the patient's respiratory patterns. Thus, average trans-thoracic impedance measurements fail to indicate the patient's level of respiratory distress that results from the recumbent position.

SUMMARY

Embodiments of the present invention address the issues discussed above and others by providing systems and methods that obtain information that allows detection of congestion by assessing the patient's respiratory distress. The respiratory distress may be assessed based on a comparison of respiration pattern before and after the patient becomes recumbent. Alternatively, the respiratory distress may be assessed by inferring distress from the amount of time the patient is able to remain in a recumbent position or the recumbent angle the patient is able to obtain.

The information related to congestion may be obtained by first detecting whether the patient is in a recumbent position. When the patient is not in the recumbent position, the respiration of the patient is monitored to detect a first respiration pattern. When the patient is in the recumbent position, the respiration of the patient is monitored to detect a second respiration pattern. Differences in the two breathing patterns may indicate respiratory distress due to the recumbent position, which is a sign of congestion.

The information related to congestion may be obtained by continuously monitoring the patient over a period of time to determine an amount of time during the period that the patient is in a recumbent position. The amount of time that the patient is in a recumbent position may indicate patient discomfort due to respiratory distress arising from the recumbent position, which is a sign of congestion.

The information related to congestion may be obtained by continuously monitoring the patient over a period of time to determine a recumbent angle that the patient is able to obtain during the period. The recumbent angle may indicate patient discomfort at greater angles approaching horizontal due to respiratory distress arising from the recumbent position, which is a sign of congestion.

DETAILED DESCRIPTION

Figure 1:
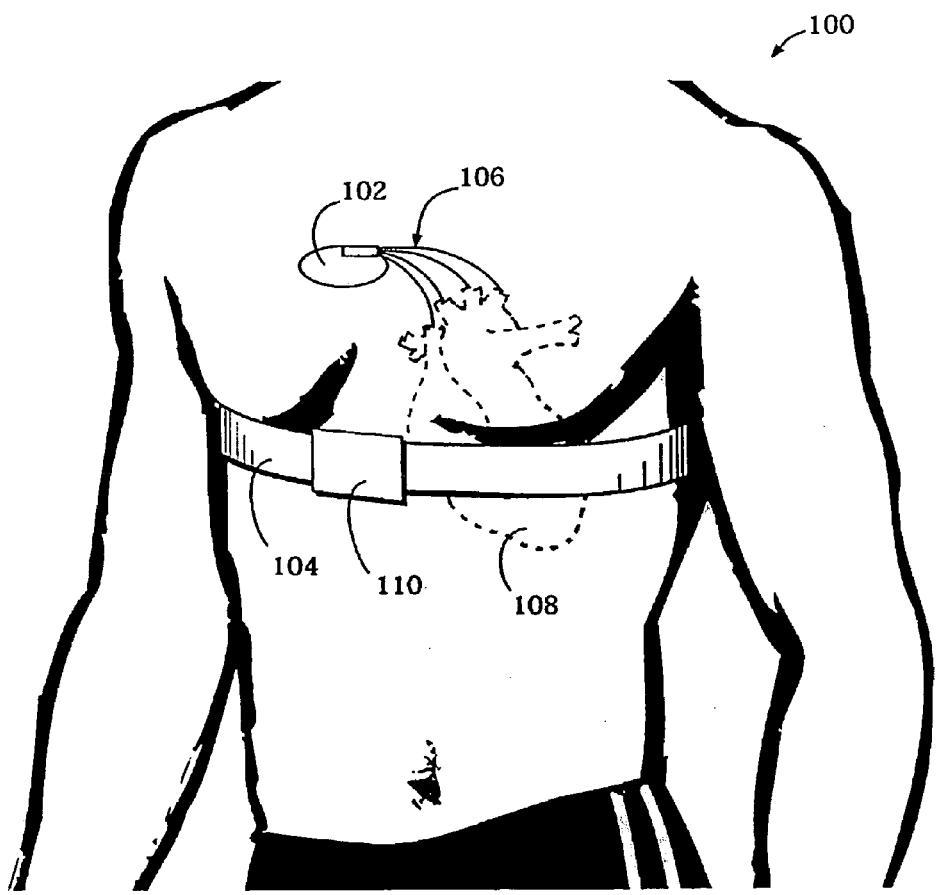
FIG. 1 illustrates one or more devices coupled to a patient to obtain information allowing the detection of congestion by monitoring the patient's response to a recumbent position.

Embodiments of the present invention attempt to obtain information related to a congestive condition and/or to diagnose a congestive condition of a patient from the information by monitoring the patient's response to a recumbent position of the patient's body. For patients suffering from congestion, respiratory distress will likely occur at some point after the patient's body achieves a recumbent state. The respiratory distress may be measured by comparison of respiratory patterns detected during the recumbent state and during a non-recumbent state. Alternatively, the respiratory distress may be detected by measuring the amount of time the patient remains recumbent and by presuming the patient is experiencing respiratory distress if the amount of time is shorter than a predetermined threshold related to a congestive condition. As another alternative the respiratory distress may be detected by measuring an angle from vertical of the patient's position and by presuming the patient is experiencing respiratory distress for greater angles of reclination if the recumbent angle is less than a normal recumbent angle FIG. 1 shows a patient's body 100 having one or more devices coupled to the body 100 to detect and/or infer respiratory distress occurring once the body 100 becomes recumbent. For example, an implantable medical device (IMD) 102 such as a pacemaker or device dedicated to congestion detection may be implanted in the body 100 and may be configured to monitor the patient's behavior in relation to a recumbent state, such as by detecting a change in respiratory patterns, finding the amount of time the patient remains in the recumbent state, or finding the recumbent angle the patient is able to obtain. Alternatively, an external device such as a respiratory effort band 104 may be coupled to the torso of the body 100 to monitor the patient's respiration in relation to the recumbent state by measuring the chest movement caused by the respiratory patterns.

In situations where an IMD 102 is utilized, the IMD 102 may make respiratory measurements as part of its routine for providing therapy to the patient, such as a pacemaker measuring respiratory rate to control pulse rate of the patient's heart 108. These respiratory measurements can also be utilized, either by the IMD 102 or another device to detect respiratory patterns of the patient. One manner of detecting the respiratory patterns is through monitoring trans-thoracic impedance variation through one or more leads 106 during each individual inhale and exhale cycle. The IMD 102 or other device coupled to the body 100 is provided with a reclination sensor, such as a tilt switch, to allow a distinction between the body 100 being in a recumbent or non-recumbent state. Furthermore, the reclination sensor may be an accelerometer to allow the recumbent angle of the patient to be measured.

In situations where an external device 104 is utilized, the external device 104 can similarly make respiratory measurements and sense the recumbent state of the body 100. For example, a respiratory effort band measures the expansion and contraction of the torso of the body 100 resulting from respiratory cycles to produce signals that represent the respiratory patterns of the patient. The external device 104 or other device also detects the reclination using a tilt switch or accelerometer to distinguish between the recumbent and non-recumbent states. The external device 104 includes a module 110 that contains electrical circuitry discussed below for obtaining information related to congestion and may also detect congestion from the obtained information.

Alternatively, the IMD 102 or external device 104 may measure the reclination of the patient and then employ a clock to track the amount of the that the body 100 is in a recumbent state. The amount of time may then be compared to a predetermined threshold to infer whether the patient has respiratory distress while in a recumbent state. The inference may be made because it may be presumed that the patient becomes non-recumbent once respiratory distress begins to occur to relieve the discomfort.

As another alternative, the IMD 102 or external device 104 may measure the recumbent angle obtained by the patient for a period of time, such as the maximum recumbent angle or an average recumbent angle that the patient achieves while sleeping The recumbent angle may then be compared to a predetermined threshold, such as a typical recumbent angle for a healthy patient, to infer whether the patient suffers respiratory distress at recumbent angles greater than the recumbent angle actually measured for the patient. The inference may be made because it may be presumed that the patient achieves the greatest recumbent angle possible while resting that does not result in discomfort due to respiratory distress.

Figure 2:
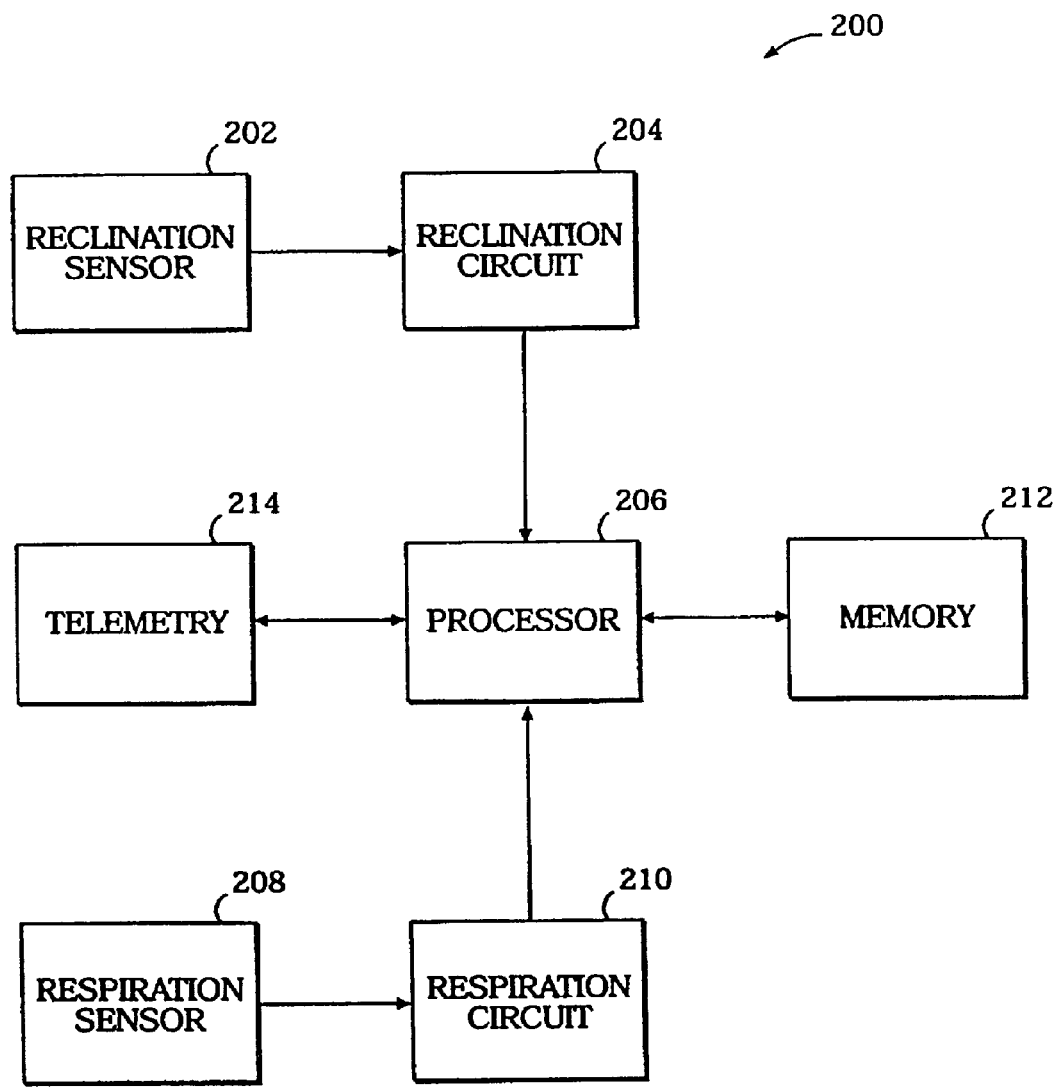
FIG. 2 shows a diagram of major components of one embodiment of a system for obtaining information allowing the detection of congestion by comparing an upright respiration pattern of the patient to a recumbent respiration pattern.

FIG. 2 shows the major components of an illustrative system 200 that detects respiratory distress caused by a recumbent position of the body 100. As discussed above, any or all of the components of system 200 may be internal or external to the body 100. For example, any or all of the components may be contained within the IMD 102 and/or module 110 of external device 104.

The system 200 includes a reclination sensor 202 the produces an electrical signal that is representative of the orientation of the reclination sensor 202 relative to gravity. One example of a reclination sensor 202 is a tilt switch. Another example is a DC accelerometer. In either case, a signal is produced by the reclination sensor 202 in response to the reclination sensor 202 having a particular orientation relative to gravity. Therefore, the reclination sensor 202 is coupled to the body 100 with a known orientation so that the reclination sensor 202 produces a detectable signal in response to the body 100 having a recumbent or non-recumbent state. The reclination sensor 202 may be multi-axis responsive so that regardless of the orientation of the body 100 while in a recumbent position (i.e., lying on back versus lying on side), a detectable signal is produced.

A reclination circuit 204 is electrically connected to the reclination sensor 202 to convert the reclination sensor signal into digital data that may be processed For a tilt switch, the conversion may be simply recognizing the switch as open or closed, where one state indicates a recumbent patient and the other state indicates a non-recumbent patient. For an accelerometer, the reclination circuit 204 may amplify and/or filter the accelerometer signal prior to conversion to digital data to maintain a sufficient granularity for more precisely determining the degree of reclination of the body 100. The reclination circuit 204 then provides the reclination data to a processing device 206 where the degree of reclination of the body 100 can be factored into the determination of congestion.

A respiration sensor 208 detects the respiration patterns of the body 100 and produces a signal representative of the respiration patterns. The respiration sensor 208 may be of various forms such as a trans-thoracic impedance sensor of an IMD 202 Other forms are possible as well, including the respiratory effort band 104 whose impedance varies as the strap 104 expands and contracts in relation to the chest of the body 100 expanding and contracting.

The signal representative of respiration is provided to a respiration circuit 210 that produces digital data from the respiration signal that can be further processed and factored into the detection of congestion. The respiration circuit 210 may amplify and/or filter the respiration signal received from the respiration sensor 208. The respiration circuit 210 then provides the respiration data that identifies the respiration pattern to the processing device 206.

The processing device 206 may be a general-purpose programmable processor, hardwired digital logic, or other suitable processing device for applying logical operations to the reclination and respiration data. One example of the logical operations of the processing device 206 are described below with reference to FIG. 3. The processor 206 utilizes memory 212 for programming and/or storage of received and processed data while implementing the logical operations of FIG. 3.

In the embodiment shown in FIG. 2, the system 200 includes telemetry 214 that allows the processor 206 to communicate information to an external device (not shown) used by the physician monitoring the patient. For example, the IMD 102 employs telemetry 214 to communicate bi-directionally and wirelessly with a device programmer An external device 104 may also employ telemetry 214 to communicate either wirelessly or through a wired connection to a device such as a programmer. The programmer may also communicate back to the device 200, such as to update instructions stored in memory 212 that are employed by the processor 206 to bring about the logical operations of FIG. 3.

Figure 3:
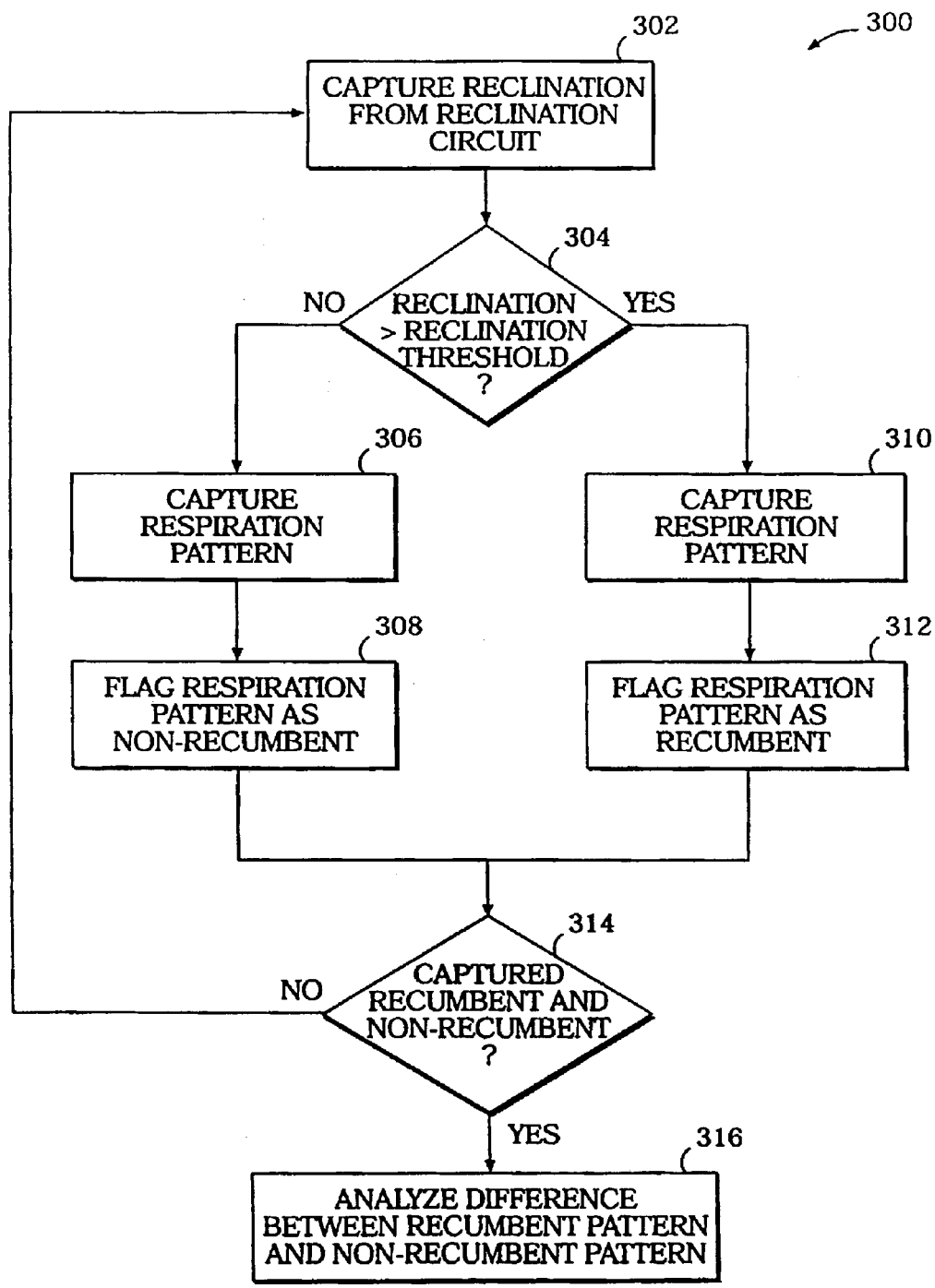
FIG. 3 shows an example of operational flow for the system of FIG. 2 for obtaining information related to congestion and for detecting congestion from the information.

The illustrative logical operations 300 of FIG. 3 are performed by the processor 206 to detect whether the patient is suffering from congestion by finding whether the respiratory distress is experienced when lying down. The logical operations begin at data operation 302 where the processor 206 receives reclination data from the reclination circuit 204. At query operation 304, the processor 206 detects whether the reclination of the torso of body 100 is greater than a reclination threshold stored in memory 212. The reclination threshold may be chosen based on the desired amount of reclination necessary to be considered recumbent. This value may be patient specific as some patients may choose to sleep or recline to different degrees. For example, reclination of at least 65 degrees away from vertical may be considered a recumbent position for one patient while reclination of at least 85 degrees away from vertical is considered a recumbent position for another.

If the reclination is not greater than the reclination threshold as determined by query operation 304, then the processor 206 accepts data form the respiration circuit 210 at data operation 306 and flags the received data as non-recumbent data at flag operation 308. If the reclination is greater than the reclination threshold as determined at query operation 304, then the processor 206 accepts data from the respiration circuit 210 at data operation 310 and flags that data as recumbent data at flag operation 312.

Query operation 314 detects whether the processor 206 has received and flagged a sufficient quantity of both recumbent data and non-recumbent data. If not, then operational flow returns to data operation 302 where the processor 206 continues to receive reclination data. If query operation 314 finds that a sufficient quantity of both recumbent and non-recumbent data have been received and flagged, then operational flow proceeds to analysis operation 316.

Figure 4:
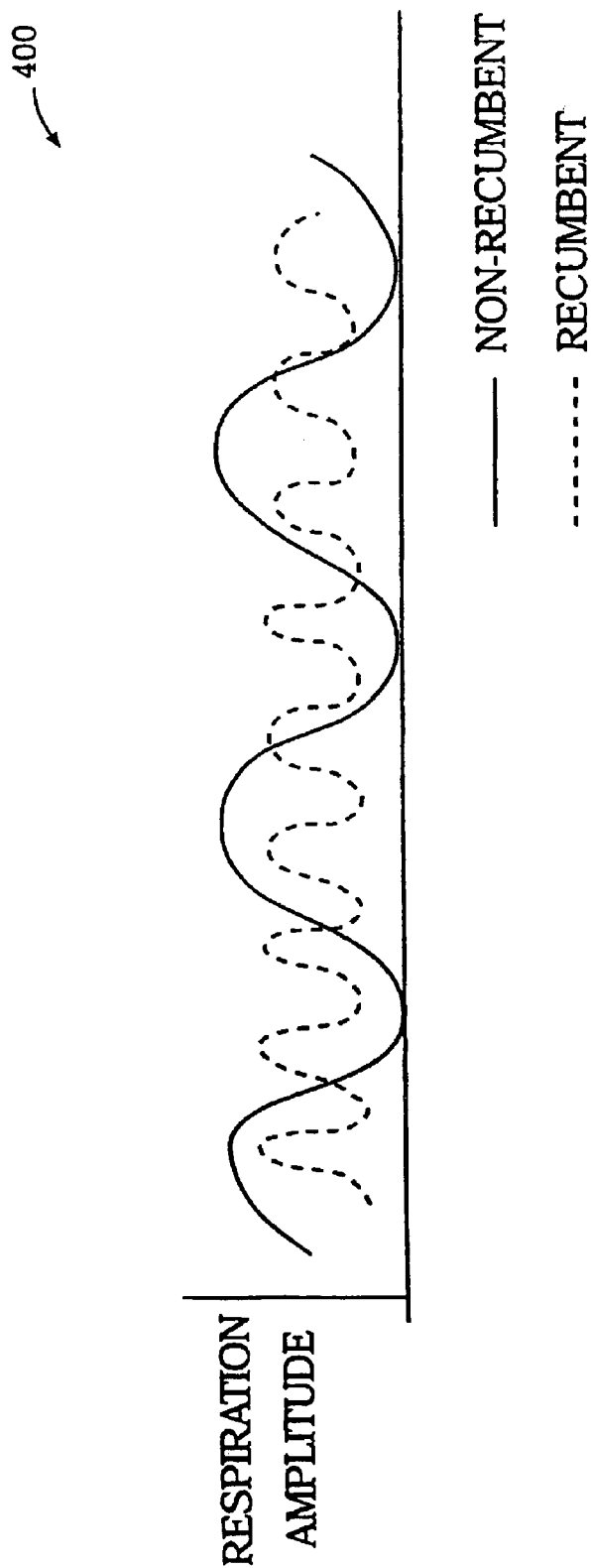
FIG. 4 depicts first and second respiration patterns whose difference indicates congestion.

At analysis operation 316, the processor 206 compares the two respiration patterns represented by the respiration data flagged as recumbent data and non-recumbent data. FIG. 4 shows two illustrative hypothetical respiration patterns. The non-recumbent respiration pattern shows that the patient is taking relatively slow and deep breaths as can be seen by the relatively low frequency and high amplitude of the pattern. However, the recumbent respiration pattern shows that the patient is taking relatively rapid and shallow breaths as indicated by the relatively high frequency and low amplitude of the pattern The rapid and shallow breathing of the recumbent respiration pattern indicates a patient suffering from orthopnea, or paroxysmal nocturnal dyspnea ("PND") that eventually occurs upon lying down.

The presence of orthopnea or PND such as shown in FIG. 4 is known to be a sign of congestion. However, other recumbent respiration pattern changes resulting from lying down may also be indicative of congestion. Therefore, at analysis operation 316 the processor 206 may perform various comparisons in addition to or as an alternative to looking for both rapid and shallow breaths. For example, the processor 206 may search for only rapid recumbent respiration relative to upright respiration. Similarly, the processor 206 may search for only shallow, or low tidal volume, recumbent respiration relative to upright respiration, As another example, the processor 206 may search for a difference in the combination of respiratory rate to tidal volume between tile recumbent and non-recumbent respiration patterns. Such a combination may be a ratio of respiratory rate to tidal volume. Additionally, the processor 206 may search for a difference in inspiration times and expiratory times, inspiration time of a recumbent pattern versus inspiratory for a non-recumbent pattern, and/or expiratory time of a recumbent pattern versus expiratory time of a non-recumbent pattern.

The results of the analysis may then be telemetered to a programmer, either in real-time or at a subsequent time, for viewing by a physician. Alternatively, for an external device an indicator such as a light emitting diode or a display screen may be included to provide direct feedback to the patient or to a physician examining the patient Although not shown in the logical operations 300 of FIG. 3, a trending operation may also be provided for the logical operations 300 so that the result of the analysis between recumbent and non-recumbent breathing patterns may be trended over time to also allow the physician to track to the progression of the patient's congestion. Furthermore, the detection of differences in breathing patterns that are indicative of congestion may be based upon difference thresholds in rate, volume, or some combination thereof. The difference thresholds may also be based upon breathing pattern differences that are known to be normal for a population so that differences beyond this threshold are considered to be an indicator of congestion. Also, the breathing pattern information, including the patterns themselves and/or any detected differences may be communicated from the medical device for review by a physician who may make the determination of whether congestion is present.

Figure 5:
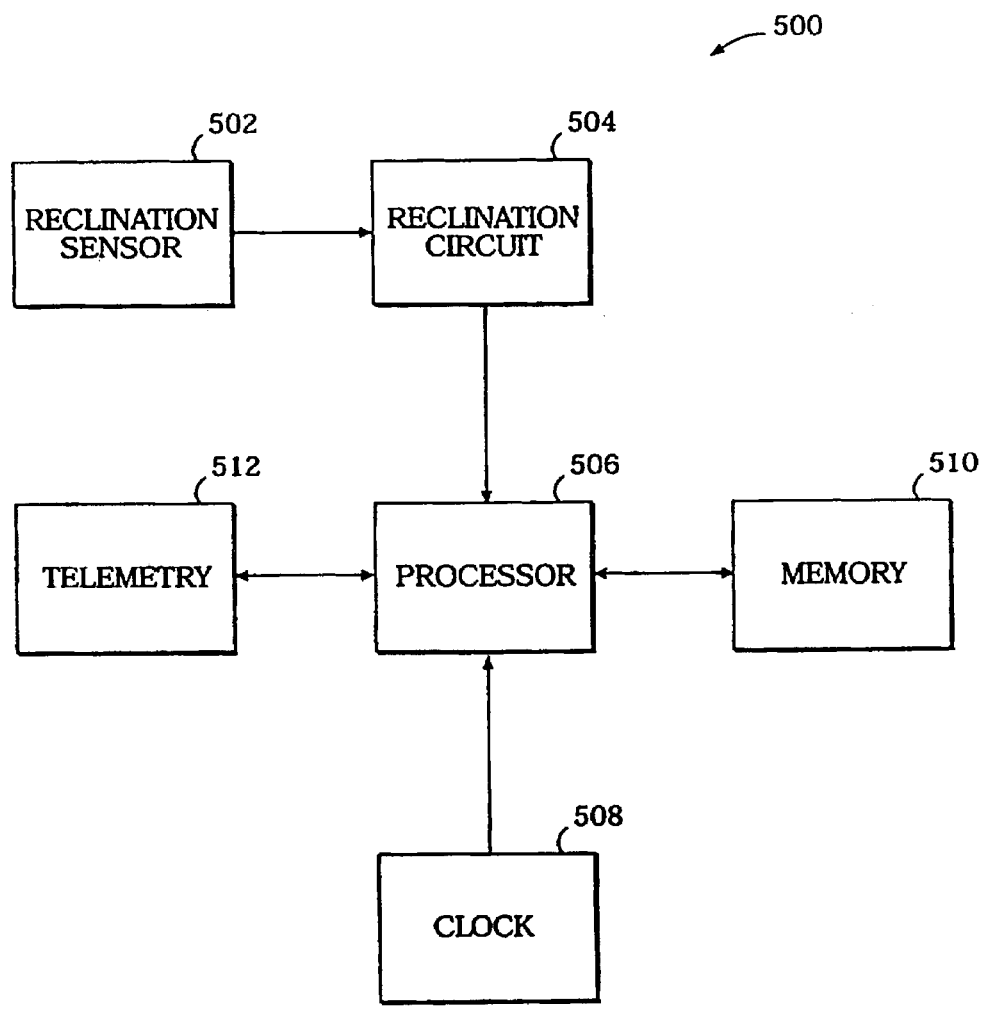
FIG. 5 shows a diagram of major components of one embodiment of a system for obtaining information allowing the detection of congestion by determining the amount of time a patient remains in a recumbent position relative to a threshold indicative of congestion and/or by determining the recumbent angle that the patient obtains relative to a threshold indicative of a normal recumbent angle.

FIG. 5 shows the major components of another illustrative embodiment of a system 500 that detects congestion by determining the amount of time a patient can remain in a recumbent position and by comparing the amount of time to a threshold related to a congestive condition. As was discussed for the system 200 of FIG. 2 any or all of the components of system 500 may be located internally or externally of the body 100. The system 500 includes a reclination sensor 502 and reclination circuit 504 as previously discussed for the system 200.

A processing device 506 such as the processing device 206 of system 200 is also included in the system 500 and receives the reclination data from the reclination circuit 504. The processor 506 utilizes the memory 510 to access programming for performing logical operations such as those discussed below with reference to FIG. 6. Additionally, the processor 506 may utilize the memory 510 to tore data describing the results of the determination of the amount of time a recumbent position can be maintained and whether a congestive condition is presumed to be present. Thus, the memory 510 can be used to maintain trending information for detecting whether the patient is experiencing congestion and whether the condition is worsening over time.

Telemetry 512 may also be included as discussed above for system 200. Telemetry 512 may be used to provide an indication to a programmer as to whether the patient is presumed to be suffering from congestion. Alternatively, the telemetry may be used to provide the amount of time the patient remains in a recumbent state to the programmer for observation by a physician. Additionally, the telemetry 512 may be used to provide an update to programming for the processor 506 that is stored in memory 510.

A clock 508 is provided to allow the processor 506 to determine how long the patient remains in the recumbent position. The clock 508 may be a simple timer circuit such as a clock used to drive the operations of the processor 506 or a more elaborate time keeping device such as a clock that maintains the actual time of day. The clock 508 provides timing data or pulses to the processor 506 that the processor 506 uses to determine time intervals.

Figure 6:
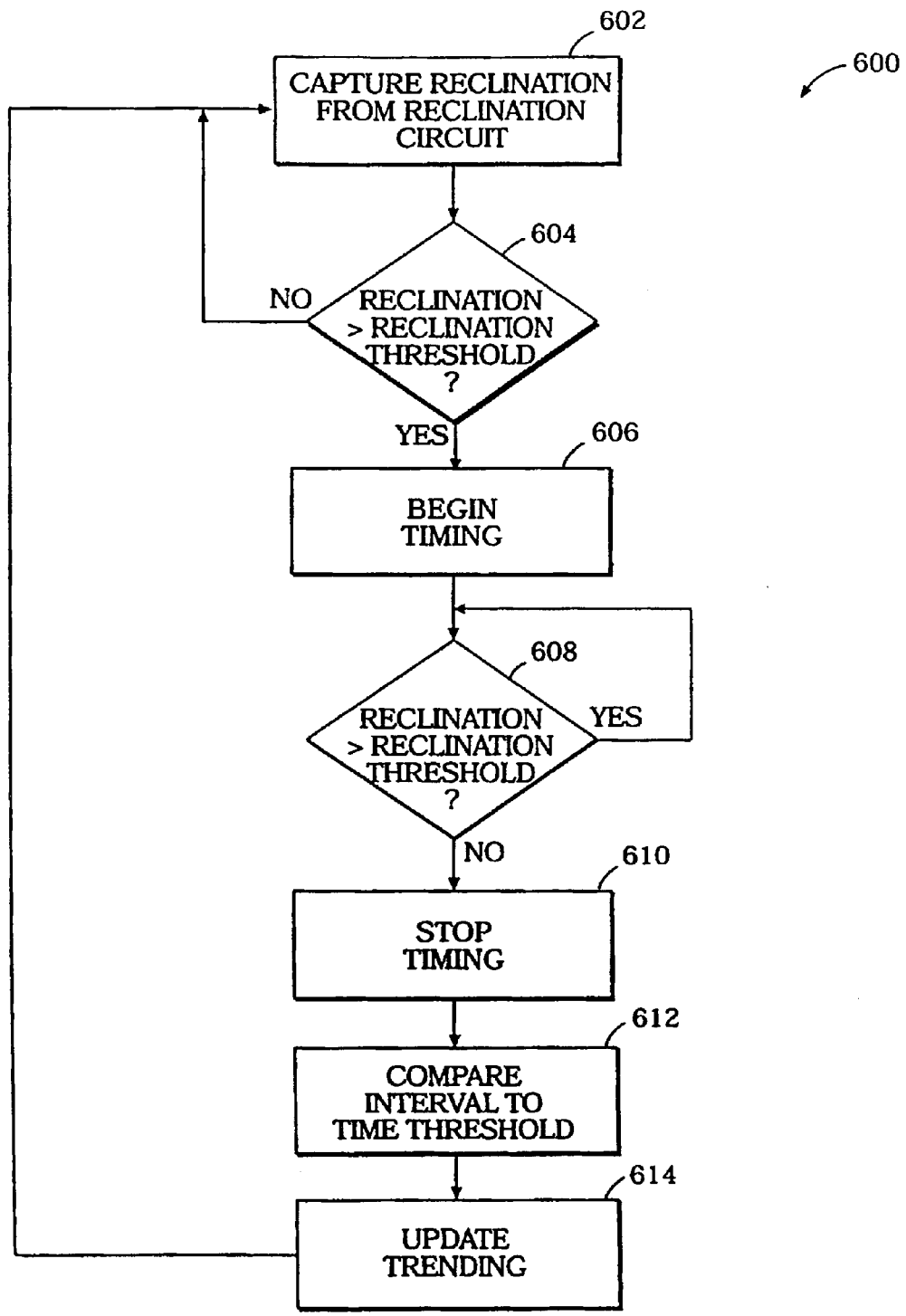
FIG. 6 shows an example of operational flow for the system of FIG. 5 to determine the amount of time that the patient remains in the recumbent position.

Illustrative logical operations 600 that are implemented by the processor 506 are shown in FIG. 6. The logical operations 600 allow the processor 506 to determine the amount of time the patient remains in the recumbent state. This determination then allows an inference to be drawn as to whether the patient is suffering from congestion brought on by respiratory distress upon lying down. The logical operations 600 begin at data operation 602 where the processor 506 receives reclination data from the reclination circuit 504.

Query operation 604 then detects whether the reclination is greater than a reclination threshold specified in memory 510. As discussed above, the reclination threshold may be patient specific as one patient may choose to lie down or sleep while reclined at an angle greater than another patient. If the reclination is not greater than the reclination threshold as determined at query operation 604, then the processor 506 receives the next set of reclination data at data operation 602. If the reclination is greater than the reclination threshold, then the processor 506 begins keeping track of time at timing operation 606 so that the interval from the time the patient became recumbent until the time the patient is upright can be found.

Query operation 608 detects whether the reclination is greater than the reclination threshold. If it is, then the patient is still recumbent, and query operation 608 repeats. If the reclination is no longer greater than the reclination threshold, then the processor 506 stops keeping track of time at timing operation 610. From the timing by the processor 506, an interval of time is known for the period when the patient was in the recumbent state.

In this embodiment, the processor 506 then compares the interval of time to a time threshold that is related to a congestive condition at comparison operation 612. This threshold may be known from a study of patients suffering from congestion who experience respiratory distress after a particular amount of time In a recumbent position Furthermore, this threshold may vary depending upon the degree of congestion that the patient is being tested for through application of the logical operations 600. Additionally, the threshold may be based upon a particular percentage of an average normal sleep time that corresponds to a particular degree of congestion, such as a patient who remains recumbent for 50% of an average normal sleep time for a population may be diagnosed as severely congested. Alternatively, the raw numbers or percentages could be trended and/or reported from the medical device to a physician who then may interpret the information to determine whether congestion is present For the embodiment shown in FIG. 6, the patient's congestion level may be trended as part of an overall wellness program. Thus, upon completion of comparison operation 612, trending information stored in memory 510 or in memory of another external device may be continuously updated based on the results of the comparison operation 612 at trend operation 614. Through these trending updates, the physician can see the progression of the patient's congestion as well as additional conditions or the patient that may be simultaneously monitored with congestion.

Figure 7:
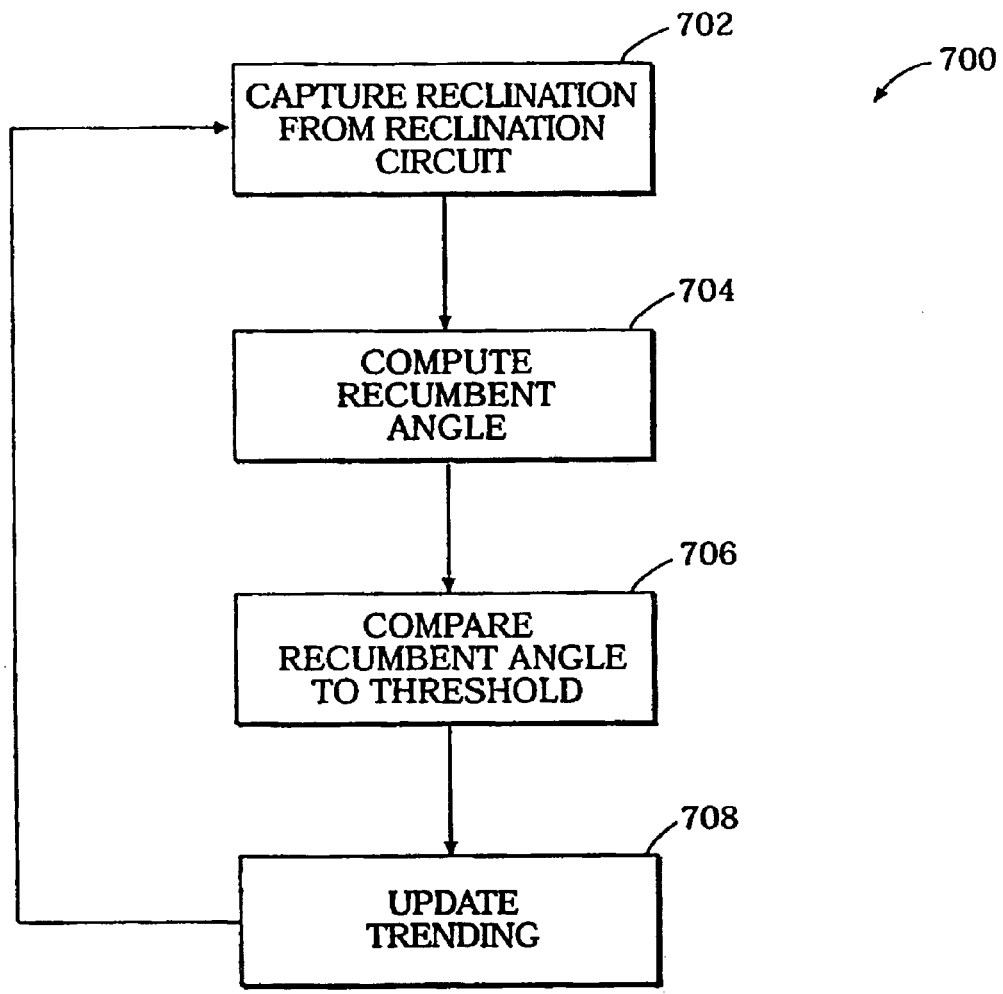
FIG. 7 shows an example of operational flow for the system of FIG. 5 to determine a recumbent angle that the patient obtains.

Illustrative logical operations 700 that may alternatively be implemented by the processor 506 are shown in FIG. 7 where the reclination sensor such as an accelerometer provides a signal that is representative of the recumbent angle rather than a signal that is merely indicative of a recumbent versus non-recumbent state. The logical operations 700 allow the processor 506 to obtain the recumbent angle that the patient is able to obtain for further processing and/or for transmission to a physician. The determined recumbent angle allows an inference to be drawn as to whether the patient is suffering from congestion brought on by respiratory distress upon reaching a degree of reclination The logical operations 700 begin at data operation 702 where the processor 506 receives reclination data from the reclination circuit 504 over a period of time. The reclination data is representative of the recumbent angle the patient obtains during the period. At process operation 704, the processor 506 computes a recumbent angle from the reclination data for the period, such as by finding the maximum recumbent angle specified by the reclination data or by averaging the recumbent angle values for the period. The period may be limited to times of day when the patient is expected or known to be resting so that there is little or no reclination data obtained while the patient is upright that would skew the average. Alternatively, a query operation may be employed by the processor 506 to throw out reclination data taken during the period that indicates an upright recumbent angle.

Comparison operation 706 then determines whether the recumbent angle is greater than a recumbent angle threshold specified in memory 510. This recumbent threshold, whose value may differ from the reclination threshold of FIG. 6, may also be patient specific as one patient may choose to lie down or sleep while reclined at a recumbent angle that is greater than another patient. If the recumbent angle is not greater than the recumbent angle threshold, then the processor 506 of this embodiment determines that the patient is suffering from congestion since it is presumed that the patient does not recline beyond the recumbent threshold due to congestion related discomfort. If the reclination is greater than the reclination threshold, their the processor 506 of this embodiment determines the patient is not suffering from congestion since it is presumed that the patient would not recline beyond the recumbent threshold due to discomfort if congestion was present.

In the embodiment of FIG. 7, the recumbent angle threshold may be know from a study of patients suffering from congestion who experience congestion once the recumbent angle is beyond a certain amount from vertical. Furthermore, this recumbent angle threshold may vary depending upon the degree of congestion that the patient is being tested for through application of the logical operations 700. Additionally, the recumbent angle threshold may be based upon a particular percentage of an average normal recumbent angle that corresponds to a particular degree of congestion, such as a patient who may only rest an a recumbent angle that is 50% of an average normal recumbent angle for a population may be diagnosed as severely congested.

For the embodiment shown in FIG. 7, the patient's congestion level may be trended as part of an overall wellness program. Thus, upon completion of comparison operation 706, trending information stored in memory 510 or in memory of another external device may be continuously updated based on the results of the computation operation 704 and/or comparison operation 706 at trend operation 708. Through these trending updates, the physician can see the progression of the patient's congestion as well as additional conditions of the patient that may be simultaneously monitored with congestion.

In another embodiment, the processor 506 may not determine whether congestion is present. Instead, the medical device may transmit the recumbent angle information to the physician who can then interpret the information to make the determination. As discussed above, the raw recumbent angle data could be trended and/or reported from the medical device to a physician who then may interpret the information to determine whether congestion is present.

While the invention has been particularly shown and described with reference to preferred embodiments thereof, it will be understood by those skilled in the art that various other changes in the form and details may be made therein without departing from the spirit and scope of the invention.

What is claimed is:

1. A method of determining whether a patient is suffering from congestion, comprising:
   detecting whether the patient is in a recumbent position;
   when the patient is not in the recumbent position, monitoring the respiration of the patient to detect a first respiration pattern;
   when the patient is in the recumbent position, monitoring the respiration of the patient to detect a second respiration pattern;
   comparing the first respiration pattern to the second respiration pattern to detect whether a difference is present between the first respiration pattern and the second respiration pattern; and
   in response to the difference between the first respiration pattern and the second respiration pattern determining whether the patient is suffering from congestion.

2. The method of claim 1, wherein detecting whether the patient is in the recumbent position comprises comparing a reclination of a torso of the patient to a threshold.

3. The method of claim 2, further comprising detecting the reclination of the torso with a tilt switch.

4. The method of claim 2, further comprising detecting the reclination of the torso with an accelerometer.

5. The method of claim 1, wherein monitoring the respiration comprises monitoring trans-thoracic impedance.

6. The method of claim 1, wherein comparing the first respiration pattern to the second respiration pattern to detect whether a difference is present comprises comparing a rate of respiration of the first pattern to a rate of respiration of the second pattern.

7. The method of claim 1, wherein comparing the first respiration pattern to the second respiration pattern to detect whether a difference is present comprises comparing a tidal volume of respiration of the first respiration pattern to a tidal volume of respiration of the second respiration pattern.

8. The method of claim 1, wherein comparing the first respiration pattern to the second respiration pattern to detect whether a difference is present comprises comparing a combination of tidal volume of respiration and respiration rate for the first respiration pattern to a combination of tidal volume of respiration and respiration rate for the second respiration pattern.

9. The method of claim 1, wherein comparing the first respiration pattern to the second respiration pattern to detect whether a difference is present comprises comparing an inspiratory time the first respiration pattern to an inspiratory time for the second respiration pattern and comparing an expiratory time the first respiration pattern to an expiratory time for the second respiration pattern.

10. The method of claim 1, further comprising:
    detecting over multiple periods whether the patient is in a recumbent position;
    when the patient is not in the recumbent position during each period, monitoring the respiration of the patient to detect a first respiration pattern for a current period; and
    when the patient is in the recumbent position during each period, monitoring the respiration of the patient to detect a second respiration pattern for a current period;
    comparing the first respiration pattern to the second respiration pattern for each period to detect whether a difference is present between the first respiration pattern and the second respiration pattern for each period; and
    analyzing the comparison for each period to determine a trend.

11. A system for determining whether a patient is suffering from congestion comprising:
    a reclination sensor that produces a reclination signal indicative of the reclination of the patient;
    detection circuitry that produces reclination data from the reclination signal;
    a respiration sensor that produces a respiration signal indicative of respiration patterns of the patient;
    respiration circuitry that produces respiration pattern data from the respiration signal; and
    a processing device that performs the following steps:
       monitoring the respiration pattern data and the reclination data,
       determining whether the patient is in a recumbent position by comparing the reclination data to data representative of a reclination threshold,
       associating the respiration pattern data obtained at a point in time with the reclination data obtained at the point in time
       comparing the respiration pattern data obtained when the patient is in a recumbent position to the respiration pattern data obtained with the patient is in a non-recumbent position to detect whether a difference is present between the respiration patterns associated with recumbent and non-recumbent positions; and
    in response to differences between the respiration patterns associated with recumbent and non-recumbent positions determining whether the patient is suffering from congestion.

12. The system of claim 11, wherein the reclination sensor is a tilt switch.

13. The system of claim 11, wherein the reclination sensor is an accelerometer.

14. The system of claim 11, wherein the respiration sensor produces a respiration signal in response to a change in trans-thoracic impedance.

15. The system of claim 11, wherein the processing device compares the respiration pattern data taken during a non-recumbent position to respiration data taken during a recumbent position to detect whether a difference in respiration rate exists.

16. The system of claim 11, wherein the processing device compares the respiration pattern data taken during a non-recumbent position to respiration data taken during a recumbent position to detect whether a difference in tidal volume of respiration exists.

17. The system of claim 11, wherein the processing device compares the respiration pattern data taken during a non-recumbent position to respiration data taken during a recumbent position to detect whether a difference in a ratio of respiration rate to tidal volume of respiration exists.

18. The system of claim 11, further comprising a communication device for transmitting the association of respiratory data with reclination data to another system.

19. A system for determining whether a patient is suffering from congestion, comprising:
- means for detecting whether the patient is in a recumbent position; and
- means for measuring a first respiration pattern while the patient is in a recumbent position and for measuring a second respiration pattern while the patient is in a non-recumbent position
- means for comparing the first respiration pattern to the second respiration pattern to detect whether a difference is present between the first respiration pattern and the second respiration pattern; and
- in response to the difference between the first respiration pattern and the second respiration pattern means for determining whether the patient is suffering from congestion.

20. The system of claim 19, wherein the means for detecting whether the patient is in a recumbent position comprises a tilt switch.

21. The system of claim 19, wherein the means for detecting whether the patient is in a recumbent position comprises an accelerometer.

22. The system of claim 19, wherein the means for measuring a first and second respiration pattern comprises a trans-thoracic impedance sensor.

23. The system of claim 19, wherein means for comparing comprises a microprocessor.

24. The system of claim 19, wherein means for comparing detects a difference in respiratory rate between the first and second respiration patterns.

25. The system of claim 19, wherein means for comparing detects a difference in tidal volume of respiration between the first and second respiration patterns.

26. The system of claim 19, further comprising a means for communicating the first and second respiration patterns to another system.

* * * * *

UNITED STATES PATENT AND TRADEMARK OFFICE
CERTIFICATE OF CORRECTION

PATENT NO. : 7,226,422 B2 Page 1 of 1
APPLICATION NO. : 10/267982
DATED : June 5, 2007
INVENTOR(S) : Hatlestad et al.

It is certified that error appears in the above-identified patent and that said Letters Patent is hereby corrected as shown below:

On the Title page, in field (57), under "Abstract", in column 2, line 11, delete "of" and insert -- or --, therefor.

In column 10, line 12 (Approx.), in Claim 11, after "congestion" insert -- , --.

Signed and Sealed this

Fourteenth Day of August, 2007

JON W. DUDAS
*Director of the United States Patent and Trademark Office*